(12) United States Patent
Furey et al.

(10) Patent No.: US 10,258,341 B2
(45) Date of Patent: Apr. 16, 2019

(54) MEDICAL ASSEMBLY AND DEVICE (71) Applicant: COOK MEDICAL TECHNOLOGIES LLC, Bloomington, IN (US)

(72) Inventors: Aidan P. Furey, Valby (DK); Palle Munk Hansen, Bjaeverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 133 days.

(21) Appl. No.: 15/370,169

(22) Filed: Dec. 6, 2016

(65) Prior Publication Data
US 2017/0079663 A1 Mar. 23, 2017

Related U.S. Application Data

(63) Continuation-in-part of application No. 15/150,471, filed on May 10, 2016.

(30) Foreign Application Priority Data

May 11, 2015 (GB) .................................. 1508005.4
May 11, 2016 (EP) .................................. 16275075

(51) Int. Cl.
*A61F 2/82* (2013.01)
*A61B 17/00* (2006.01)
*A61B 17/12* (2006.01)

(52) U.S. Cl.
CPC .... *A61B 17/12113* (2013.01); *A61B 17/1214* (2013.01); *A61B 17/12118* (2013.01);
(Continued)

(58) Field of Classification Search
CPC .......... A61B 17/12145; A61B 17/1215; A61B 17/12177; A61B 17/1204;
(Continued)

(56) References Cited

U.S. PATENT DOCUMENTS 6,221,100 B1 * 4/2001 Strecker .................... A61F 2/90
623/1.22
6,312,421 B1 11/2001 Boock
(Continued)

FOREIGN PATENT DOCUMENTS

WO  WO 1996/041589    12/1996
WO  WO 2004/021933     3/2004
(Continued)

OTHER PUBLICATIONS

Combined Search and Examination Report for GB Application No. GB1508005.4, dated Nov. 12, 2015.

*Primary Examiner* — Jocelin C Tanner
(74) *Attorney, Agent, or Firm* — Brinks Gilson & Lione (57) ABSTRACT

A medical filler delivery assembly includes a micro catheter for delivering filler material such as filamentary material into an aneurysm in a vessel, the assembly also including a positioning mechanism which includes a support element made of knitted wires, as well as an expansion mechanism for expanding the support element within the vessel. The wires form an array of polygonal, preferably rhomboidal cells, the wires being intertwined at their junctions by at least one turn around one another, the intertwined regions extending in the longitudinal direction of the support element. The support element is able to trap the micro catheter in position and in practice such that its distal end is disposed within the aneurysm sac.

12 Claims, 8 Drawing Sheets

(52) U.S. Cl.
CPC .. *A61B 17/12131* (2013.01); *A61B 17/12168* (2013.01); *A61B 17/12172* (2013.01); *A61B 17/12181* (2013.01); *A61F 2/82* (2013.01); *A61B 17/1204* (2013.01); *A61B 17/12136* (2013.01); *A61B 17/12186* (2013.01); *A61B 2017/00867* (2013.01); *A61B 2017/1205* (2013.01); *A61F 2002/823* (2013.01)

(58) Field of Classification Search
CPC ........ A61B 17/12113; A61B 17/12118; A61B 17/12131; A61B 17/12136; A61B 17/1214; A61B 17/12168; A61B 17/12172; A61B 17/12181; A61B 17/12186; A61B 2017/00867; A61B 2017/1205; A61F 2/82; A61F 2002/823
See application file for complete search history.

(56) References Cited

U.S. PATENT DOCUMENTS

| | | | |
|---|---|---|---|
| 6,440,098 B1 | 8/2002 | Lüscher | |
| 6,569,190 B2 | 5/2003 | Whalen, II et al. | |
| 6,589,199 B1 | 7/2003 | McCrory et al. | |
| 6,780,196 B2 | 8/2004 | Chin et al. | |
| 7,875,044 B2 | 1/2011 | Feller, III et al. | |
| 8,597,320 B2 | 12/2013 | Sepetka et al. | |
| 2005/0119684 A1* | 6/2005 | Guterman | A61B 17/12022 606/198 |
| 2005/0240261 A1 | 10/2005 | Rakos et al. | |
| 2006/0147483 A1 | 7/2006 | Chaouk et al. | |
| 2007/0043432 A1* | 2/2007 | Perouse | A61F 2/07 623/1.36 |
| 2007/0270941 A1* | 11/2007 | Headley | A61F 2/90 623/1.38 |
| 2011/0046716 A1 | 2/2011 | Parkinson et al. | |
| 2011/0264132 A1* | 10/2011 | Strauss | A61B 17/12022 606/194 |
| 2011/0319917 A1 | 12/2011 | Ferrera et al. | |
| 2012/0091171 A1 | 4/2012 | Lovelace, III et al. | |
| 2012/0316632 A1 | 12/2012 | Gao | |
| 2014/0277097 A1* | 9/2014 | Castleberry | A61B 17/12145 606/200 |
| 2014/0343663 A1* | 11/2014 | Sudin | A61M 29/02 623/1.15 |

FOREIGN PATENT DOCUMENTS

| | | |
|---|---|---|
| WO | WO 2006/044632 | 4/2006 |
| WO | WO 2009/124288 | 10/2009 |
| WO | WO 2011/003147 | 1/2011 |

* cited by examiner

MEDICAL ASSEMBLY AND DEVICE

RELATED APPLICATIONS

This application is a continuation-in-part of U.S. patent application Ser. No. 15/150,471, filed May 10, 2016, which application claims the benefit of priority of Great Britain Patent Application No. GB 1508005.4, filed on May 11, 2015, and claims the benefit of priority to European Patent Application No. 16275075.6, filed May 11, 2016, which application claims the benefit of priority of Great Britain Patent Application No. GB 1508005.4, filed on May 11, 2015, all of which are incorporated by reference here in their entireties.

TECHNICAL FIELD

The present invention relates to medical devices and to an aneurysm treatment assembly comprising such a device and in particular an assembly able to deliver into an aneurysm sac a filler material such as, but not limited to, a filament or coil. Embodiments of the invention can be used to deliver filler material to other locations, such as into a vessel of other cavity.

BACKGROUND OF THE INVENTION

There are several medical conditions which can benefit from implantation into a patient of a filler material, an embolization or other device, whether temporary or permanent. Examples include the closure of blood vessels or other lumens. Another example for which such procedures can be particularly useful is in the treatment of aneurysms, where a part of a vessel wall weakens and then expands outwardly to create an enlarged zone of the vessel, often having the form of a sac. This vessel expansion occurs as a result of blood pressure and tends to continue due to further and progressive weakening of the vessel wall. If left untreated, persistent pressure from the blood flow on the weakened wall tissue can lead to eventual rupture of the vessel and consequential haemorrhaging. Treatments for aneurysms have therefore focused on reducing the pressure on the weakened vessel wall, for instance by diverting blood flow or by isolating the weakened vessel wall, for instance by means of a stent graft. Another treatment method involves filling the aneurysm sac with a filler material which stops the flow of blood into the sac and therefore stops or substantially reduces the pressure on the weakened walls. The filler may be an embolization coil, which will cause blood therearound to clot and thus close the sac and provide a protective barrier to prevent blood flowing into the sac and thereby to prevent rupture of the weakened section of the vessel. In other instances, the aneurysm sac may be filled with a biocompatible material, such as a hydrogel or a polysaccharide fibre, which may be of a biodegradable nature. A biodegradable filler performs the same function as an embolization coil, that is to fill the aneurysm sac and provide pressure protection to the weakened vessel walls, with the additional advantage of allowing remodeling of the vessel wall over time. Moreover, biodegradation of the filler will ensure that no foreign matter remains in the patient's vessel after conclusion of the treatment.

Such fillers and coils can also be used to close off a vessel or other lumen in a patient.

The process of introducing such a filler or coil into a patient can take time, particularly given that this is often carried out remotely from the aneurysm by an endoluminal procedure. There is also the risk that the filler material can escape from the aneurysm sac, not only during the filling procedure but also after. It has been postulated that this can be avoided by implantation of a stent or stent graft across the aneurysm, though this entails leaving in the patient a foreign object. It has also been postulated to use a balloon to close off the aneurysm while it is being filled but this entails the closure of the vessel, which necessarily reduces the amount of time the balloon can remain in the vessel.

Examples of prior art devices and methods can, for instance, be found in US2012/0316632, U.S. Pat. Nos. 6,780,196, 8,597,320, 7,875,044, US2012/091171, U.S. Pat. Nos. 6,569,190, 6,312,421, US2006/0147483, U.S. Pat. Nod. 6,589,199, 6,440,098, WO2011/003147, US2011/319917, WO2009/124288, US2005/119684, US2011/046716, and WO2006/044632.

There are other medical applications in which a wire member can be employed having particular characteristics in response to applied forces. Medical devices falling into this category include stents, filters and devices for retrieving blood clots, especially from the brain. A device for implantation inside a patent is disclosed in WO-96/41589 in which rhombus-shaped wire cells have intertwined regions which extend in the circumferential direction of a tubular element.

SUMMARY OF THE INVENTION

The present invention seeks to provide an improved assembly for delivering filler material into a patient and in the preferred embodiments into a vessel or aneurysm sac.

According to an aspect of the present invention, there is provided a medical filler delivery assembly for delivering filler material into a vessel of a patient including:

an elongate delivery catheter including a proximal end, a distal end and a lumen therein, the lumen including an exit aperture located at or proximate the distal end of the catheter and an inlet aperture located at or proximate the proximal end of the catheter, the lumen being for delivery of filler material; and a positioning mechanism including an elongate carrier including a proximal end and a distal end, the carrier including a tubular support element of knitted wire at the distal end thereof and an expansion mechanism coupled to the support element for expanding the knitted support element, the support element being positioned or positionable adjacent the distal end of the catheter, wherein expansion of the support element provides a support barrier adjacent the exit aperture of the catheter, characterized in that the support element comprises a plurality of wire elements intertwined with one another to form a plurality of polygonal-shaped cells, the wire elements being intertwined with one another at the junctions of the cells by at least one turn around one another, the wire elements passing through their intertwined regions in the longitudinal direction of the tubular member.

The support element, being made of wire, can be of a very open construction allowing the continued flow of fluid, for instance blood, within the vessel. The knitted structure of the support element, it has been found, can impart sufficient forces on the vessel, particularly useful in holding filler material in place, as well as the delivery catheter, until the later has settled in position.

In the preferred embodiment, the support element is formed of a plurality of wire elements intertwined one with another. Intertwining of the wires can produce an open yet strong structure. The intertwined wires may be coupled to one another by at least one turn around one another, preferably at least two or at least three turns around one another.

Advantageously, the knitted wire forms a plurality of open cells delimited by wire sections. The cells may have a polygonal shape, for instance a generally rhomboidal or diamond shape, found to be most efficient in terms of providing an open structure and in terms of support strength.

In a practical embodiment the positioning mechanism includes an elongate carrier having a proximal end and a distal end, a tubular element slidably disposed on the elongate carrier and including a proximal end and a distal end, and a fixing member located at the distal end of the elongate carrier, the support element being attached at one end to the fixing member and at the other end to the distal end of the tubular element, wherein sliding of the tubular element towards the fixing member causes radial expansion of the support element.

Preferably, the wires of the support element are twisted around one another adjacent their attachments to the tubular element and the fixing member, able to optimise the flow of fluid through the support element when deployed.

The support element may include a substantially cylindrical body portion and may include generally conical end portions.

The support element is preferably radially collapsible, advantageously by longitudinal elongation thereof.

In practical embodiments, the support element may be made from stainless steel or shape memory material. It may be made from shape memory alloy.

The wires of the support element may be monofilament wires or multifilament wires.

In the preferred embodiment, the assembly includes a carrier sheath within which the delivery catheter and the positioning mechanism are slidably disposed.

According to another aspect of the present invention, there is provided a method of delivering filler material into a body of a patient including:

positioning a distal end of an elongate delivery catheter at a body location to be filled, the catheter including a lumen therein for delivery of filler material and an exit aperture at or proximate the distal end of the catheter;

locating a distal end of a positioning mechanism alongside the distal end of the delivery catheter, the positioning mechanism including an elongate carrier, the carrier including a support element of knitted wire at the distal end thereof and an expansion mechanism coupled to the support element for expanding the knitted support element, and expanding the support element so as to provide a support barrier adjacent the exit aperture of the catheter.

In one procedure, the distal end of the delivery catheter is positioned into an aneurysm sac and the support element is disposed across the aneurysm sac.

Preferably, the support element applies pressure against the distal end of the delivery catheter when deployed.

According to another aspect of the present invention, there is provided a medical device comprising a plurality of wire elements intertwined with one another to form a plurality of substantially rhomboidal cells arranged in the form of a tubular member, the wire elements being intertwined with one another at the junctions of the cells by at least one turn around one another, characterized in that the wire elements pass through their intertwined regions in the longitudinal direction of the tubular member.

This arrangement facilitates the application of longitudinal forces to the tubular member, and in particular to the uniform distribution of such forces.

The dimension of each cell in the longitudinal direction of the tubular member is preferably greater than the dimension in the circumferential. This assists in the distribution of forces in a desired manner.

Other aspects and advantages of the teachings herein will become apparent form the description of the preferred embodiments which follows.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Various embodiments of medical filler delivery assembly are described below and shown in the accompanying drawings. It is be understood that the drawings are schematic only and are not intended to show the various components of the assembly to scale. In many cases, the assembly has been depicted in enlarged form for the sake of clarity of disclosure. The skilled person will appreciate that the assembly may be configured to a variety of different sizes, and shapes, in order to correspond to the vessel or other organ in which the device is to be deployed.

The preferred embodiments are particularly useful for the neurovascular vessels such as the carotid artery, the vertebral artery and so on. The invention is not so limited as the teachings herein can be used for other body vessels.

Figure 1:
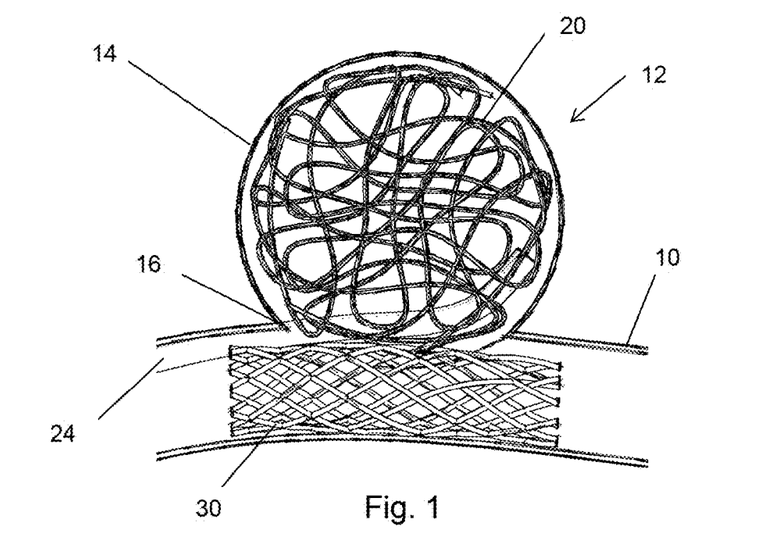
FIG. 1 is a schematic diagram of an example of a filler delivery arrangement using a support stent.

Referring first to FIG. 1, this shows a schematic diagram of a vessel 10 having developed an aneurysm 12, in the form of an aneurysm sac 14 which extends to one side of the vessel 10 and opens into the vessel 10 at its neck 16. If the aneurysm 12 is left untreated, blood pressure will generally result in the sac 14 continuing to grow, resulting in continued weakening of the vessel wall and eventual rupture of the vessel, leading to haemorrhaging, with potentially serious consequences on the patient.

The treatment depicted in FIG. 1 involves delivering into the aneurysm sac 14 one or more lengths of filamentary material 20. The material of 20 may be platinum coil, for instance. The purpose of the filamentary material 20 is to take up the volume in the aneurysm sac, in other words to fill it, and as a result reduce the amount of blood able to flow into the sac 16 and as a consequence reduce the blood pressure on the walls of the sac 14. In the case of the use of platinum coil or other filamentary material, the material 14 causes an embolic reaction within the aneurysm sac, as a result sealing the aneurysm from the flow of blood. The material 20 may not completely fill the volume inside the sac 14 and may instead rely on embolization to fill the sac 14 completely.

The filamentary material 14 may be delivered by means of a micro catheter 24, from a suitable source of material, not shown in FIG. 1.

In order to hold the micro catheter 24 in place, as well as the filamentary material 20, the example in FIG. 1 uses a stent 30 positioned across the aneurysm 12 and in particular across the neck 16. The stent 30, which may be of any suitable design, will generally remain in place within the vessel 10 even after the procedure. While the use of a stent 30 can provide good support for the micro catheter 24 and retention of the distal end 25 of the micro catheter 24 during the delivery process as well as retention of the filler material 20 within the aneurysm sac 14, the arrangement leaves within the body a foreign object, that is the stent 30. While there are many medical instances where it is advantageous to retain a stent permanently within a patient's body, for example to keep a vessel open and stop its collapse, it is generally preferred not to leave foreign objects within the body for any length of time, as foreign objects can cause undesirable side effects such as restenosis.

Figure 2:
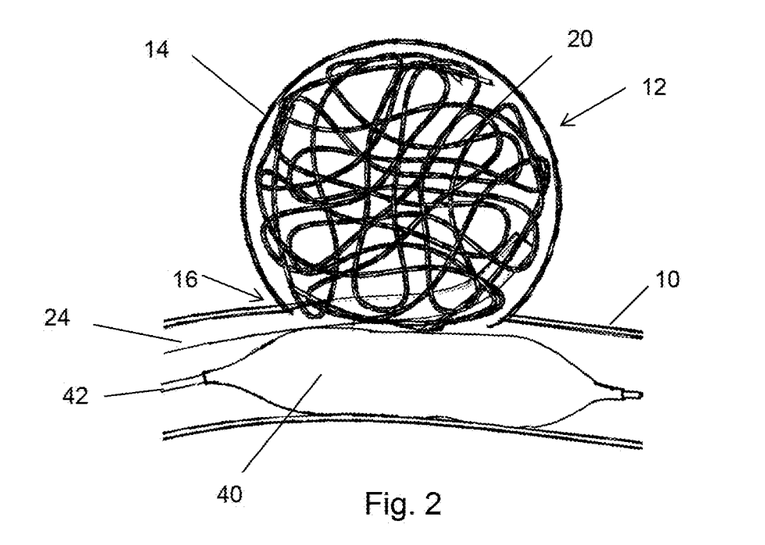
FIG. 2 is a schematic diagram of an example of a filler delivery arrangement using a support balloon.

Referring now to FIG. 2, this shows another example of arrangement for treating an aneurysm 12 within the wall of a vessel 10, again by delivering into the aneurysm sac 14 filamentary material 20 via a micro catheter 24. The material 20 and micro catheter 24 may be the same as the example of FIG. 1.

In place of a retention stent 30, the arrangement of FIG. 22 uses an expandable balloon 40 for trapping the micro catheter 24 such that its distal end remains within the aneurysm sac 14 during the delivery process, as well as for keeping the filamentary material 20 within the aneurysm sac 14 and preventing its unintentional escape. The balloon 40 is typically carried on a balloon catheter 42, which includes a suitable inflation lumen and a port into the chamber of the balloon 40, as is well known in the art.

The use of an inflatable balloon 40 avoids the disadvantage of the arrangement of FIG. 1, namely of implanting into the patient's vessel a permanent or semi-permanent foreign object. However, the balloon 40 does not readily permit the flushing from the aneurysm sac 14 of the fluid used to deliver the filler material 20. Furthermore, the balloon 40 will, during the period in which it is deployed, stop the flow of fluid through the vessel 10. As a result of this, the filler delivery process must necessarily be shorter, with the result that the material 20 is not trapped within the aneurysm sac 14 by the retention mechanism (in this instance the balloon 40) for as long as might be desirable. This can lead to incomplete fixation of the filamentary material 20 within the aneurysm sac 14, for example as a result of incomplete embolization of blood within the sac 14. It is known to have donut shaped balloons 40, which have a central lumen passing though the balloon, however lumens of this nature still create a substantial constriction within the vessel 10.

Figure 3:
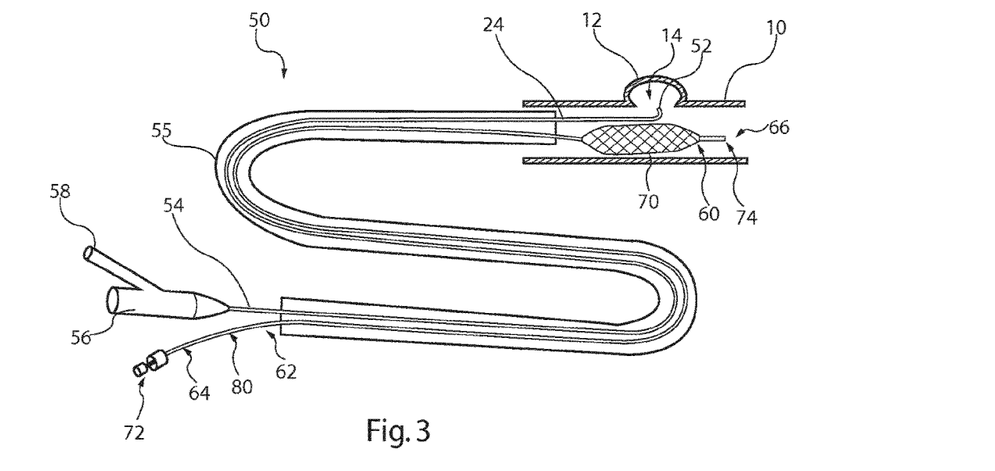
FIG. 3 is a schematic diagram of an embodiment of a medical filler delivery assembly.

Referring now to FIG. 3, this shows in schematic form an embodiment of an assembly for delivering filler material into an aneurysm sac 14. The assembly 50 includes a micro catheter 24 of similar type to that shown in the arrangements of FIGS. 1 and 2 and which is in effect an elongate tube having a lumen therein for feeding filler material through to its distal end 52, which in this instance is at the extremity of the micro catheter 24. The micro catheter 24 has a proximal end 54 which is attached to a source 56 of filler material. The source 56 includes a chamber within which filler material can be stored and includes a feed port 58 for coupling to a source of pressurized fluid, typically saline solution. The filler material could be any suitable filler and in this example is preferably a filamentary material.

The filamentary material could be of any type deemed suitable for performing the medical function and could be sub intestine submucosa (SIS), polysaccharide, a biocompatible polymeric thread or other biocompatible material. Specific examples, though the disclosure herein is not limited to these, include: woven polyester (e.g. DACRON®), polyamide (e.g. Nylon), expanded polytetrafluoroethylene (ePTFE; e.g. GORE-TEX®); bioremodelable materials such as: extracellular matrix material (ECM) for instance submucosa, renal capsule membrane, dermal collagen, dura mater, pericardium, fascia lata, serosa, peritoneum and basement membrane layers. Examples of submucosa include: intestinal submucosa, including small intestinal submucosa, stomach submucosa, urinary bladder submucosa and uterine submucosa.

The micro catheter 24 can be used to deliver a variety of filler materials, not necessarily only filamentary materials. The filler could, for instance, be in the form of short lengths of material, pellets, or the like.

The assembly 50 also includes a positioning mechanism 60 which is formed of an elongate carrier 62 having a proximal end 64 and a distal end 66. A tubular support element 70 in the form of a basket, of knitted wire as described in further detail below, is attached to the elongate carrier 62 at the distal end 66. An expansion mechanism 72, 74, described in further detail below, causes the support element 70 to expand radially outwardly, whereupon the support element 70 presses against the distal end 52 of the micro catheter 24 in order to hold the latter in position, as well as providing support for any filler material 20 which is fed into the sac 14 of the aneurysm 12, as described in further detail below.

The elongate carrier 62 is typically formed of a catheter 80 and a wire, rod or inner catheter 82 which is slidably disposed within a lumen of the catheter 80. Further details of the preferred embodiment are described in connection with FIG. 4 in particular.

Figure 5:
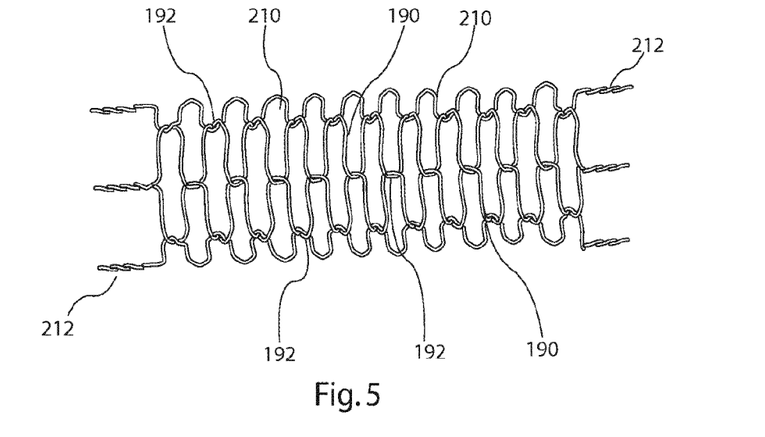
FIGS. 5 to 10 show different embodiments of knitted wire blanks for the support structure taught herein.
Figure 6:
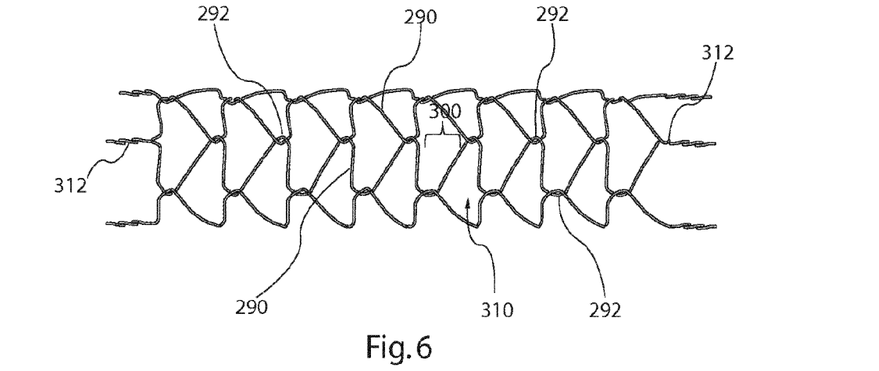
Figure 7:
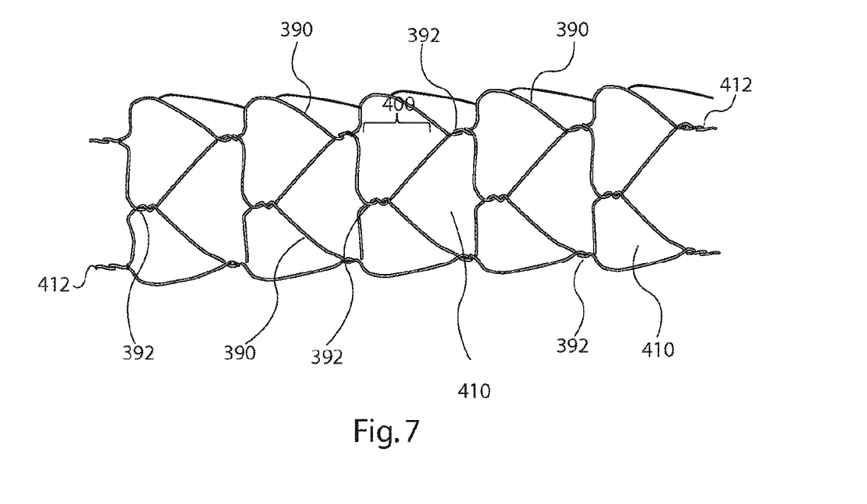

As will be apparent from FIG. 3, as well as from FIGS. 5 to 7, the knitted wire support element 70 is disposed across the neck 16 of the aneurysm sac 14 during the deployment procedure and can also be left for a period after termination of the stage in which filler material is fed into the aneurysm sac, which can enable the filler material 20 to settle in the sac 14, for instance but not necessarily until embolization has occurred. For example, the wire support element 70 can be left in place for 15 minutes or longer, for instance up to one hour.

The assembly 50 preferably also includes an outer sheath 55 in which the delivery catheter 24 and the support member 70/80 are held for deployment into the patient's vessel.

Figure 4:
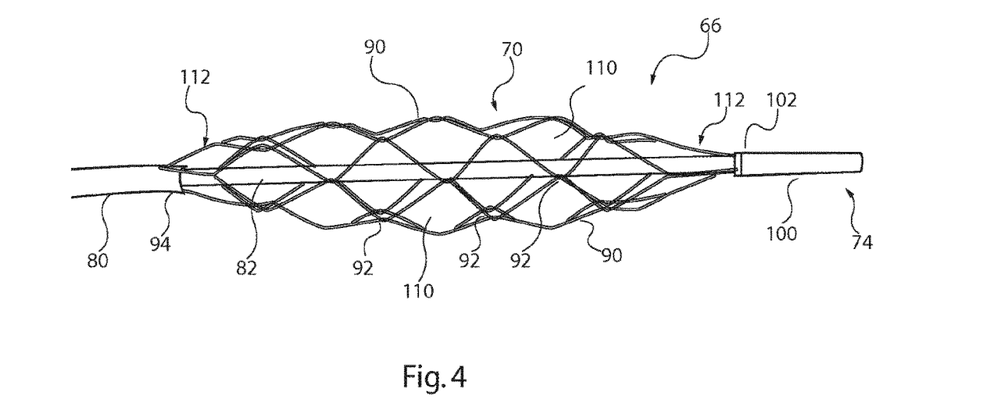
FIG. 4 is a schematic diagram of an expandable knitted support element of the assembly of FIG. 3.

FIG. 4 shows an enlarged view of the knitted wire support element 70 of this embodiment. The wire support element 70 is formed of a plurality of wires 90 which are intertwined with one another at junction or crossing points 92. This intertwining is preferably in the form of wrapping or twisting of two wires 90 together for at least one turn, though more preferably for at least two to three turns or more of the wires, in order to tie the wires 90 to one another. There are provided a plurality of wires 90, which extend generally in the longitudinal direction of the support element 70, from the distal end 94 of the support catheter 80 to the proximal end 102 of a fixation element 100 of the expansion mechanism.

In the embodiment of FIG. 4, there are provided four pairs of wires 90 around the circumference of the distal end 94 of the support catheter 80 and the proximal end 102 of the fixation element 100, though any other suitable number of wire pairs may be used. The wires 90 are arranged so as to create a series of open cells 110 within the structure of the support element 70. As will be apparent in particular from FIG. 4, the cells 110 are formed by portions or sections of the wires 90 between the intertwined crossing points 92. In the embodiment shown the cells have a polygonal shape, formed by the wire sections between four crossing points 92. The cells 110 in the embodiment of FIG. 4 could be said to have a generally rhomboidal or diamond shape, although in other embodiments could have a different shape. The sides of the cell are preferably substantially equal in length so that each cell forms a rhombus.

At the ends of the support element 90, the wires are wrapped around one another in pairs, shown at 112, so as to provide in this embodiment four intertwined wire pairs extending generally in the longitudinal direction of the basket 70. The wire pairs are fixed either to the distal end 94 of the support catheter 80 or to the proximal end 102 of the fixation element 100 in any suitable manner, such as by tying, knotting, welding, bonding or the like. Wrapping the ends of the wires in the manner shown at 112 in FIG. 4 gives the support structure 70 a very open configuration even at the points at which this tapers towards the support catheter 80 and fixation element 100. At the ends 112, the wire pairs can be wrapped together over numerous turns, dependent primarily on the desired length of the support element 70, its intended expanded diameter, the degree by which it is desired to create an open structure, the number of wires used, as well as the desired length of the intertwined portions 112 of the wire pairs.

The support element 70 can be made of wires of stainless steel, or a shape memory material such as Nitinol or any other suitable material. It is also envisaged that the wires may also be in the form of a hybrid structure which incorporates a radiopaque element. A suitable structure may include an extruded Nitinol tube, which envelopes a wire the outside diameter of which is equivalent to the inside diameter of the tube. The radiopaque core could be of any of the following: platinum, palladium, gold, tantalum or other radiopaque material.

The wires 70 are preferably monofilament wires but in other embodiments could be of multifilament strands. Each wire 90 preferably has a diameter in the region of 0.020 millimeters to 0.15 millimeters, preferably about 0.020 millimeters to about 0.1 millimeters, the latter being particularly suitable for neurological applications. Practical examples used in neurological applications had wires of 0.08 millimeters in diameter.

The structure of the support element 70 is not to be restricted to the example shown in FIG. 4 and any other suitable knitted wire structure may be used, other examples being shown in FIGS. 5 to 10 described below.

The use of a knitted wire structure for the support element 70, it has been found, can be produce a structure which generates much higher opening forces when expanded, which can as a result provide much better retention of the distal end of the delivery catheter 24 into an aneurysm and also much better retention of filler material 20 within the aneurysm sac 14. Furthermore, the open structure of the support element impinges little on the flow of fluid, blood typically, in the patient's vessel, allowing the support element 70 to remain deployed in the vessel for longer periods than, for instance, a balloon based retention assembly.

The fixation element 100 may be a portion of tubing similar to that of the support catheter 80 but which is fixed to inner elongate element 82. The fixation element 100 could, though, be of any structure able to hold the distal end of the support element 70. The inner elongate element 82 could be a wire, rod, micro catheter, or any other suitable device.

The support catheter 80 is slidable on the inner elongated element 82 and in particular towards and away from the fixation element 100, which is fixed to the inner elongated element 82. As a result, when the support catheter 80 is pulled back (proximally), or similarly the inner element 82 pushed distally, the distance between the distal end 94 of the support catheter 80 and the proximal end 102 the fixation element 100 increases, causing the support element 70 to elongate and in practice to contract radially onto the inner element 82. On the other hand, when the support catheter 80 is pushed forwards (distally), or conversely the fixation element 100 is pulled proximally, the distance between the distal end 94 of the support catheter 80 and the proximal end 102 of fixation element 100 shortens, which results in a shortening and consequential radial expansion of the support element 70. The radial expansion can be achieved by use of spring material for the wires 90 but can equally be achieved by the relative stiffness of the wires 90 and their knitted arrangement, which will cause the intertwined wire cells to expand outwardly on longitudinal compression of the element 70. Typically, the preferred embodiments will use a combination of these two characteristics in order to cause the support element 70 to expand radially.

It is preferred that the support element 70 has a substantially cylindrical section or body portion having a generally uniform diameter, with tapering ends. Other embodiments, though, may have other shapes, for instance a generally curved longitudinal, tapering or other profile to the body portion of the support element 70.

FIGS. 5 to 10 show other examples of knitted structures for the support element 70. Referring first to FIG. 5, the embodiment shown has a plurality of wires 190 which are intertwined with one another at junction or crossing points 192 and are also intertwined with one another in pairs at the ends of the structure 212. In this example, the structure differs from the example shown in FIG. 4 in that the portions of wire 190 between junctions or crossing points 192 are substantially perpendicular to the longitudinal axis of the frame. This provides a structure in which the cells 210 are narrower than the example of FIG. 4, that is in which the gaps between adjacent wire sections 190 is smaller. In a practical example, the space between adjacent wire sections 190 may be in the region of 0.50 mm and the overall diameter of the support structure, when in the expanded condition is 4 mm.

Referring now to FIG. 6, this shows another example of wire structure for the support element 70. In this embodiment, the wires are knitted so as to create what could be described as triangular cells 310 along the body portion of the structure, formed by the wire portions 290 and the intertwined junction or crossing points 292. As a result, from each crossing point 292, there are two wire portions 290 extending substantially perpendicularly to the longitudinal axis of the frame and two wire sections extending at an angle to the longitudinal axis, in this example at an angle of around 55° to the longitudinal axis. Again, at the ends of the structure, pairs of wires are intertwined together as shown at 312. In this example, the gap between aligned junction points 292, depicted by reference numeral 300 in FIG. 6, may be in the region of 1.7 mm. the frame has, in this example, an expanded diameter of around 4 mm.

FIG. 7 shows a structure for the support element 70 which is very similar to the structure shown in FIG. 6, save for the fact that the wire portions 390 extending at an angle to the transverse axis of the structure are at an angle of around 40° to the longitudinal axis. The gap 400 between adjacent aligned crossing points 392 is, in this example, 2.3 mm for a frame having a diameter of around 4 mm when expanded. The wire sections 390 form open cells 410, which are larger than the cells 310 of the example of FIG. 6.

Figure 8:
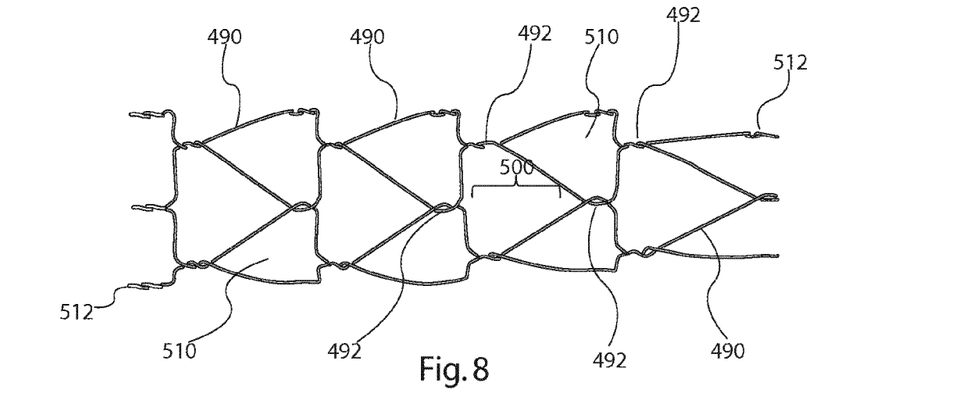

FIG. 8 shows another example of structure again very similar to the structures shown in FIGS. 6 and 7, the primary difference being the angle at which the wire sections 490 extend from the crossing points 492, this being in the region of 35° to the longitudinal axis of the structure. As with the examples of FIGS. 6 and 7 two of the wire sections 490 extend from the crossing points in a direction substantially perpendicular to the longitudinal axis. In the example shown in FIG. 8, the gap 500 between adjacent crossing points 492 is in the region of 3.1 mm for a frame having an expanded diameter of around 4 mm.

As with the other examples, the wires are intertwined in pairs 512 at the ends of the body portion of the frame. The structure also has open cells 510 which are, as with the examples of FIGS. 6 and 7, of generally uniform size along the length of the body portion of the structure.

Figure 9:
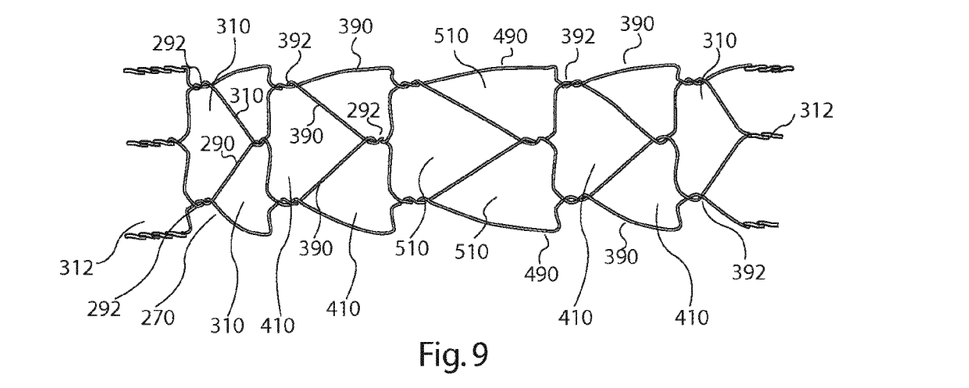

Referring now to FIG. 9, this shows a structure for the support element 70 which could be described as an amalgamation of the structures shown in FIGS. 6 to 8, specifically having intertwined wires which provide different size cells along the length of the structure. In this example, at the ends of the body portion, the cells have wire portions 290 and crossing points 292 with pairs of the wires 290 having the angles of the example of FIG. 6. Adjacent the cells 310, in a direction towards the centre of the structure, there are cells 410 formed of wire portions 390 having the characteristics of the example of FIG. 7, whereas at the centre of the structure, there are cells 510 formed of wire portions 490 having the characteristics of the example of FIG. 8. Thus, the structure shown in FIG. 9 will provide different characteristics along its length. Where the cells are smaller, as at the ends of the structure shown in FIG. 9, the wires will impart a greater opening force on the vessel, whereas in the centre of the structure of FIG. 9, the wires will impart a smaller opening force. The skilled person will appreciate that a support structure 70 could be devised having different cell structures in an arrangement different from that of FIG. 9 and specifically designed for a particular clinical need.

Figure 10:
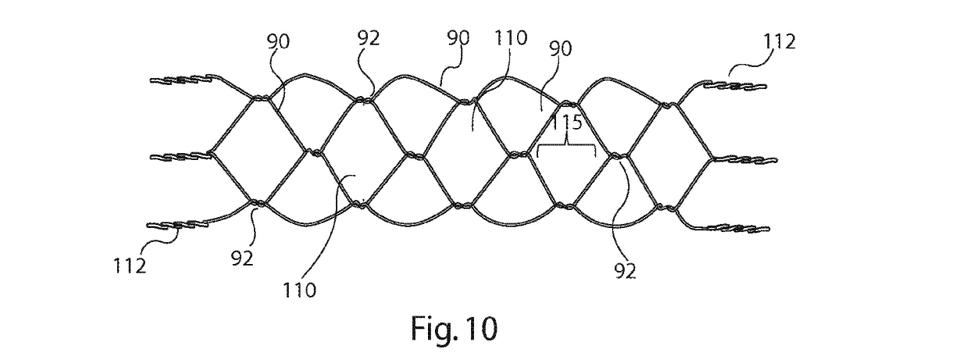

FIG. 10 shows a wire blank similar to FIGS. 5 to 9 but which forms the support structure 70 shown in FIG. 4. In this example, the wire portions 90 are at an angle of around 55° relative to longitudinal axis of the structure and the gap 115 between adjacent lined crossing points 92 is in the region of 2.2 mm for a structure having an expanded diameter of around 4 mm.

As with all of the examples of FIGS. 5 to 10, the intertwined wire pairs 112 at the end of the body portion will be attached to the catheter 80 and fixation element 100 in the manner shown in FIG. 4.

Each of the cells 110 in FIGS. 4 to 10 has a dimension 'x' in the longitudinal direction of the support element and a dimension 'y' in the circumferential direction as shown in FIG. 10.

In preferred embodiments, the dimension x is greater than dimension y, so that the angles directed towards the end of the support element (i.e. towards the left and right of FIG. 10) are smaller than the angles pointing in the circumferential direction (i.e. towards the top and bottom of FIG. 10). This provides a flexible arrangement with good resistance to the formation of kinks. It provides a uniform compressive force in the longitudinal direction of the cell pattern and facilitates a homogeneous and stable construction.

However, there may be applications in which 'y' is greater than 'x'. This may be suitable if a higher radial force is desired with increased flexibility in the longitudinal direction.

The regions in which the wires 90, 190, 290, 390, 490 and 590 are intertwined with one another extend in the longitudinal direction of the respective support element.

Figure 11:
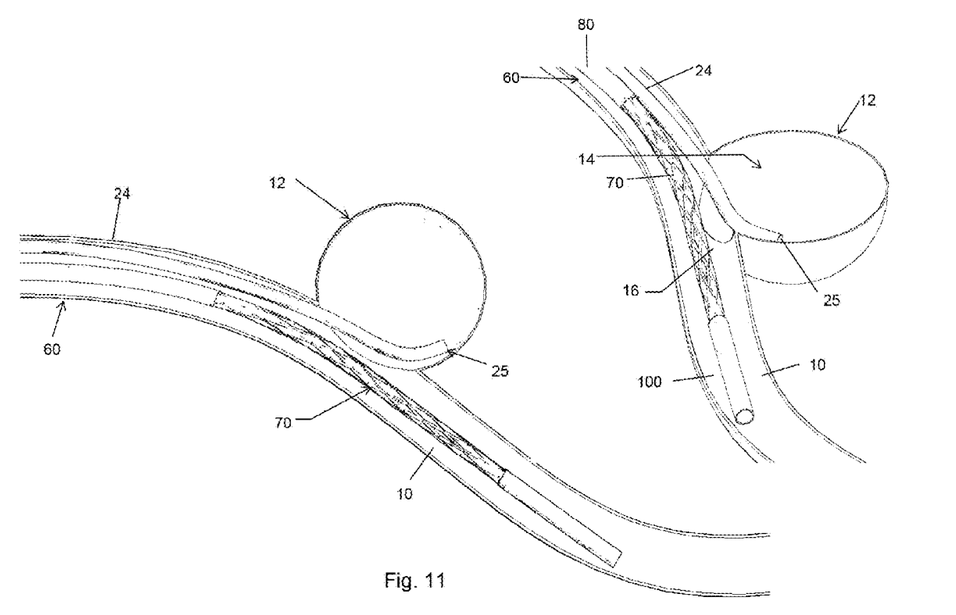
FIG. 11 is a is a schematic diagram of an assembly as taught herein positioned alongside an aneurysm to be treated.

Referring now to FIG. 11, this shows the first stage of delivery of filler material into an aneurysm 12. The distal end 25 of the micro catheter 24 is positioned within the aneurysm sac 14 and for this purpose, the distal end will usually be curved or bent so as to facilitate its positioning within the aneurysm sac 14. Typically, an aneurysm 12 will occur on the outside of the curved portion of a vessel, as depicted in the Figures, which will also assist in locating the distal end 25 of micro catheter 24 into the aneurysm 12 as a result of the general tendency of the micro catheter 24 to remain straight.

The positioning mechanism 60 is also located within the vessel 10 such that the support element 70 extends across the aneurysm 12 and specifically across the neck 16 of the aneurysm, most preferably positioned so that the body portion of the support element 70 is located adjacent to neck 16 of the aneurysm 12. At this stage, the support element 70 is longitudinally elongated and radially contracted, so as to sit relatively tightly over the inner element 82, by maximising the gap between the support catheter 80 and fixation element 100.

The micro catheter 24 and positioning mechanism 60 may be deployed into the vessel 10 at the same time, or they could be deployed at different times, for example by positioning the micro catheter 24 first and then inserting the positioning mechanism 60 second, or vice versa.

Figure 12:
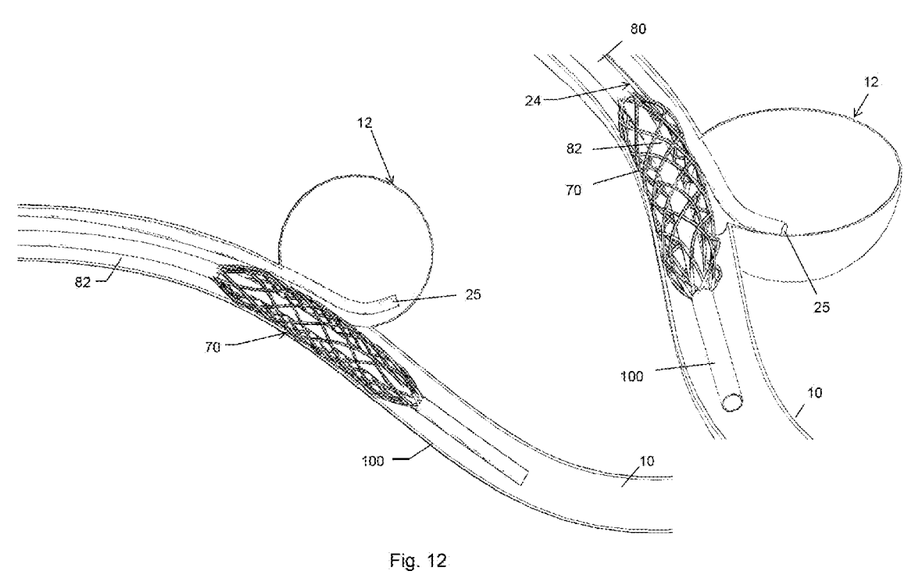
FIG. 12 is a is a schematic diagram of the assembly of FIG. 11 with the support element expanded to trap the delivery catheter in position.

FIG. 12 shows the second stage of the procedure, in which the support catheter 80 is pushed forwardly (distally), or the fixation element 100 is pulled proximately, so as to cause the knitted wire frame 70 of the support element to expand radially outwardly, as shown in FIG. 12. This has the effect of trapping the micro catheter 24 and specifically its distal end 25 in the aneurysm 12. Trapping the distal end 25 of the micro catheter 24 in this manner is important because the filler feeding stage, typically carried out under pressure, will generate a rebound force on the distal end of the micro catheter 24, which could in the absence of retention cause the distal end 25 to move out of the aneurysm sac 14, which would result in a failed procedure. As explained above, the knitted, intertwined structure of the wires forming the support element 70 can impart substantial retaining force onto the micro catheter 24 in order to keep its distal end 25 properly in place.

The support element 70 can be repositioned during this stage, for instance to ensure precise positioning relative to the aneurysm 12, by stretching the support element 70 again to contract it radially, which allows it to be repositioned prior to being expanded again. In this manner, the support element 70 can be positioned accurately across the neck 16 of the aneurysm 12.

Figure 13:
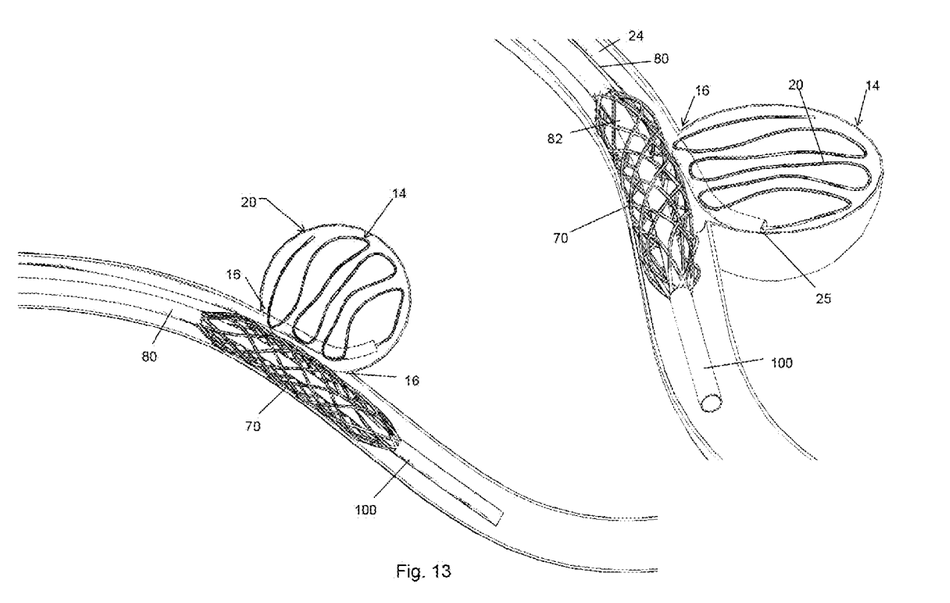
FIG. 13 is a is a schematic diagram of the assembly of FIG. 11 with the support element expanded and the delivery catheter withdrawn.

Referring now to FIG. 13, with the support element or basket 70 still in the expanded condition, filler material 20, in this example filamentary material, is fed from the source 56 through the lumen of the micro catheter 24, out of its distal end 25 and into the volume of the aneurysm sac 14, thereby to fill the aneurysm sac. The amount of filler material fed into the aneurysm sac 14 will be dependent upon a number of factors. Often, the volume of filler material will be substantially less than the volume of the aneurysm sac as the mechanism relies upon embolization of blood within the aneurysm sac, which is promoted by the filler material 20, to create a volume of solid material within the aneurysm thereby to block it off from the blood flow within the vessel 10. In some embodiments, though, the filler material 20 is injected to a volume substantially equivalent to the internal volume of the aneurysm sac, in which case the mechanism relies upon the filler material 20 per se to block the aneurysm.

As explained above, retaining the support element 70 in the expanded condition during this stage of the process ensures not only that the distal end 25 of the micro catheter 24 remains in place even with the back force generated by the filling pressure, but also acts as a barrier across the neck 16 of the aneurysm 12, in order to keep the filler material 20 within the aneurysm sac during this stage of the process.

Once a sufficient amount of filler material 20 has been injected into the aneurysm sac 14, the micro catheter 24 can be removed. In some cases, the micro catheter 24 will be removed prior to removal of the support element 70 (in which case support element could be partially collapsed radially to remove holding pressure on the micro catheter 24 before being expanded fully again). In other embodiments, the micro catheter 24 and the positioning mechanism 60 can be withdrawn substantially simultaneously, in which case the support element 70 will be regularly retracted (by pushing the inner element 82 distally or pulling the support catheter 80 proximally or a combination of the two). This loosens the pressure on the micro catheter 24 enabling then both components to be withdrawn from the vessel 10.

Figure 14:
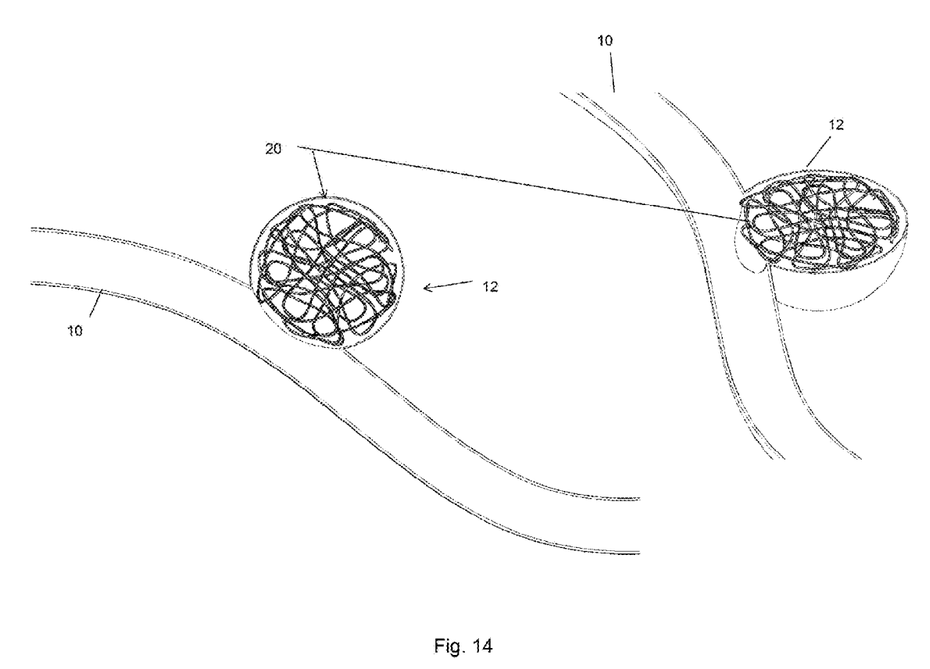
FIG. 14 is a is a schematic diagram of the vessel after treatment and removal of the filler delivery assembly.

Once withdrawn, as shown in FIG. 14, the filler material 20 remains within the aneurysm sac to close off the aneurysm 12, whereupon blood flow through the vessel 10 regains a natural flow as if the aneurysm did not exist.

With reference to FIGS. 12 and 13, it can be seen that the open structure of the support element 70, even when expanded within the vessel 10, provides little restriction to the flow of blood through the vessel 10, enabling the assembly to be used in a large variety of vessels for treating aneurysms and also allowing a longer procedure to ensure proper occlusion of an aneurysm without having to compromise in respect of deployment times. Moreover, effective support can be provided during the aneurysm occlusion process without the need for a permanent implant in the form of a vascular stent, flow diverter or the like. The open structure of the support element 70 also means that it can be disposed across branch vessels as blood can flow through the open cells 110 as well as in the longitudinal direction of the support element 70.

It will be appreciated that the use of a wire basket also allows flushing fluid to be expelled from the aneurysm sack 14 during the delivery of the filler material 20, which enables more filler material 20 to be administered into the aneurysm sack 14.

The embodiments described above have a support structure 70 formed of a single layer of knitted wires. Other embodiments may have two layers of knitted wires, one interposed over the other and preferably off-set, such that the open cells of one knitted wire layer are positioned above or below (respectively) the wire portions of the overlying or underlying wire layer. As a result, the openings within the double structure can be smaller. In such examples, the wires may be of a smaller diameter than those used for a single layer knitted structure.

In the embodiments described above, the knitted wire structure 70 is formed of eight wires which are knitted together. Other embodiments may use a different number of wires, for example 12 or 16 wires or more and equally with fewer wires, such as six. These would similarly be arranged in pairs of wires at the ends, although it is not excluded that three or more wires could be intertwined together at the ends of the structure rather than being intertwined in pairs as shown in the embodiments described above.

The embodiments described above use a support structure 70 formed solely of wires. It is envisaged, though, that in some embodiments there may be provided a sleeve disposed over the wire structure, formed of a porous fabric material, such as an ultra-high molecular weight polyethylene, for instance Dyneema™. It is preferred that such a sleeve is made of stretchable material. The sleeve will be open at its ends to allow fluid to pass through the structure during the deployment of the device.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A medical filler delivery assembly for delivering filler material into a vessel of a patient, the assembly comprising:
   an elongate delivery catheter comprising a proximal end, a distal end, and a lumen therein, the lumen comprising an exit aperture located at or proximate the distal end of the catheter and an inlet aperture located at or proximate the proximal end of the catheter, the lumen being for delivery of filler material; and
   a positioning mechanism comprising an elongate carrier comprising a proximal end and a distal end, the carrier comprising a tubular support element at the distal end thereof, the tubular support element being radially expandable, the support element being positioned or positionable adjacent the distal end of the catheter, wherein expansion of the support element provides a support barrier adjacent the exit aperture of the catheter,
   the support element comprising a plurality of wire elements intertwined with one another to form a plurality of polygonal-shaped cells, the wire elements being intertwined with one another at junctions of the cells by at least one turn around one another, the wire elements passing through their intertwined regions in a longitudinal direction of the tubular support element, a dimension of each cell in a circumferential direction of the tubular support element being greater than a dimension in the longitudinal direction.

2. The assembly of claim 1, wherein the cells have a substantially rhomboidal shape.

3. To the assembly of claim 1, wherein the wire elements are intertwined with one another by at least two turns around one another at each junction.

4. The assembly of claim 1, wherein the wire elements are intertwined with one another by at least three turns around one another at each junction.

5. The assembly of claim 1, wherein the positioning mechanism includes an elongate carrier having a proximal end and a distal end, a tubular element slidably disposed on the elongate carrier and comprising a proximal end and a distal end, and a tubular fixing member located at the distal end of the elongate carrier, the support element being attached at one end to the tubular fixing member and opposite the distal end of the tubular element, wherein sliding of the tubular element towards the tubular fixing member causes radial expansion of the support element.

6. The assembly of claim 5, wherein the wire elements of the support element are twisted around one another adjacent their attachments to the tubular element and the tubular fixing member.

7. The assembly of claim 1, wherein the support element is radially collapsible by longitudinal elongation thereof.

8. The assembly of claim 1, comprising a filler storage unit coupled to the inlet aperture of the catheter, the unit containing filamentary material.

9. The assembly of claim 1, wherein the tubular support element comprises a knitted element.

10. A medical device comprising a plurality of wire elements intertwined with one another to form a plurality of substantially rhomboidal cells arranged in the form of a tubular member, the wire elements being intertwined with one another at junctions of the cells by at least one turn around one another, wherein the wire elements pass through their intertwined regions in a longitudinal direction of the tubular member, the dimension of each cell in a circumferential direction of the tubular member being greater than the dimension in the longitudinal direction.

11. The device of claim 10, wherein the wire elements are intertwined with one another by at least two turns around one another.

12. The device of claim 10, wherein the wire elements are intertwined with one another by at least three turns around one another.

* * * * *